(12) United States Patent
Brooks, Jr.

(10) Patent No.: US 11,494,809 B2
(45) Date of Patent: Nov. 8, 2022

(54) SYSTEM FOR TARGET ONLINE ADVERTISING USING BIOMETRIC INFORMATION

(71) Applicant: BioBrand, LLC, Fort Worth, TX (US)

(72) Inventor: James G. Brooks, Jr., Fort Worth, TX (US)

(73) Assignee: BioBrand LLC, Fort Worth, TX (US)

( * ) Notice: Subject to any disclaimer, the term of this patent is extended or adjusted under 35 U.S.C. 154(b) by 0 days.

(21) Appl. No.: 17/077,452

(22) Filed: Oct. 22, 2020

(65) Prior Publication Data

US 2021/0090128 A1   Mar. 25, 2021

Related U.S. Application Data

(60) Provisional application No. 62/926,224, filed on Oct. 25, 2019.

(51) Int. Cl.

| | |
|---|---|
| *G06Q 30/02* | (2012.01) |
| *G16H 50/70* | (2018.01) |
| *G06N 20/00* | (2019.01) |
| *G16H 40/67* | (2018.01) |
| *G06V 40/20* | (2022.01) |
| *G06V 40/16* | (2022.01) |
| *G16H 20/60* | (2018.01) |
| *G16H 20/30* | (2018.01) |

(52) U.S. Cl.
CPC ......... *G06Q 30/0269* (2013.01); *G06N 20/00* (2019.01); *G06Q 30/0201* (2013.01); *G06Q 30/0246* (2013.01); *G06Q 30/0254* (2013.01); *G06Q 30/0258* (2013.01); *G06Q 30/0277* (2013.01); *G06V 40/174* (2022.01); *G06V 40/20* (2022.01); *G16H 40/67* (2018.01); *G16H 50/70* (2018.01); *G16H 20/30* (2018.01); *G16H 20/60* (2018.01)

(58) Field of Classification Search
CPC ........... G06Q 30/0201; G06Q 30/0246; G06Q 30/0254; G06Q 30/0258; G06Q 30/0277; G06Q 30/0269
See application file for complete search history.

(56) References Cited

U.S. PATENT DOCUMENTS

| | | |
|---|---|---|
| 8,725,567 B2 | 5/2014 | Huang et al. |
| 9,361,623 B2 | 6/2016 | Angell et al. |

(Continued)

*Primary Examiner* — Azam A Ansari
(74) *Attorney, Agent, or Firm* — Whitmyer IP Group LLC

(57) ABSTRACT

An apparatus for providing customized advertisements includes a database that stores a plurality of electronic advertisements, receives biometric information of a client from at least one biometric device of the client, and receives receptivity information of the client responding to the plurality of electronic advertisements, as well as a processor that accesses the database, and maps the biometric information and the receptivity information and analyzes the mapped information to generate customized marketing data. The processor also calculates a receptivity probability for each of the plurality of electronic advertisements based on the customized marketing data by using current biometric state of the client, selects an electronic advertisement from the plurality of electronic advertisements based on the calculated receptivity probabilities, and outputs to the client the selected electronic advertisement.

19 Claims, 2 Drawing Sheets

(56) References Cited

U.S. PATENT DOCUMENTS

| | | |
|---|---|---|
| 2008/0155587 A1 | 6/2008 | Sokola et al. |
| 2010/0324992 A1 | 12/2010 | Birch |
| 2012/0072289 A1 | 3/2012 | Pradeep et al. |
| 2014/0122231 A1 | 5/2014 | Slutsky et al. |
| 2014/0323817 A1* | 10/2014 | El Kaliouby .......... G16H 20/40 600/300 |
| 2016/0012292 A1* | 1/2016 | Perna ...................... G06F 3/013 382/117 |

\* cited by examiner

SYSTEM FOR TARGET ONLINE ADVERTISING USING BIOMETRIC INFORMATION

TECHNICAL FIELD

The present teachings relate generally to a system for target advertising, and more particularly to a system for target online advertising using biometric information.

BACKGROUND

Traditionally, it takes seven times to repeat a marketing message before audiences register and accept the message. Further, social media target advertisements based merely on conversations. For example, Amazon may target ads based on verbal conversations that Alexa hears. Ads can also be targeted based on social media posts that a person writes and shares. There is a need to make target advertising more effective.

SUMMARY

The needs set forth herein as well as further and other needs and advantages are addressed by the present teachings, which illustrate solutions and advantages described below.

It is an object of the present teachings to remedy the above drawbacks and shortcomings associated with known marketing systems.

It is also an object of the present teachings to provide effective targeted advertising by taking into account when audiences are receptive to advertisements in general or advertisements for particular products or services, and/or receptive to particular forms of advertisements.

It is another object of the present teachings to provide effective targeted advertising that cuts through the "noise" of other advertisements and thus increases the potential for getting a person's attention. The term "noise" has a negative connotation in marketing and means anything that distracts an audience member from receiving a message being conveyed in a marketing campaign. Promotional clutter is a major issue in that a person tires of it and has a difficult time remembering specific messages.

It is another object of the present teachings to provide improved target advertising by utilizing biometric information of audience members.

These and other objects of the present teachings are achieved by providing an apparatus and/or system that targets advertisements to audiences by utilizing their biometrics, for example but not limited to their heartbeat, sleep patterns, steps walked or ran, location, water intake, food intake, etc. The apparatus uses biometric information on an audience member to gauge emotional and/or physiological receptivity toward marketing messages (e.g., brand messages). For instance, the apparatus looks at one or a combination of: a person's heart rate (current as compared to base), sleep pattern, steps walked/jogged/ran during the day, water intake, and/or food intake, in order to determine when advertising is most effective for that person. The biometric information may also be paired with the person's emotions as detected and assessed by facial recognition technology in order to provide optimum target advertising that is personalized to the person's current mood.

The present teachings provide an apparatus comprising a database storing a plurality of electronic advertisements (e.g., Internet advertisements), receiving biometric information of a client from at least one biometric device of the client, and receiving receptivity information of the client responding to the plurality of electronic advertisements, as well as a processor accessing the database, mapping the biometric information and the receptivity information, and analyzing the mapped information to generate customized marketing data, calculating a receptivity probability for each of the plurality of electronic advertisements based on the customized marketing data by using current biometric state of the client, selecting an electronic advertisement from the plurality of electronic advertisements based on the calculated receptivity probabilities, and outputting to the client the selected electronic advertisement.

Other teachings of the apparatus, system and method are described in detail below and are also part of the present teachings.

For a better understanding of the present teachings, together with other and further aspects thereof, reference is made to the accompanying drawings and detailed description, and its scope will be pointed out in the appended claims. The summary is not intended to limit the scope of the present teachings.

DETAILED DESCRIPTION

Figure 1:
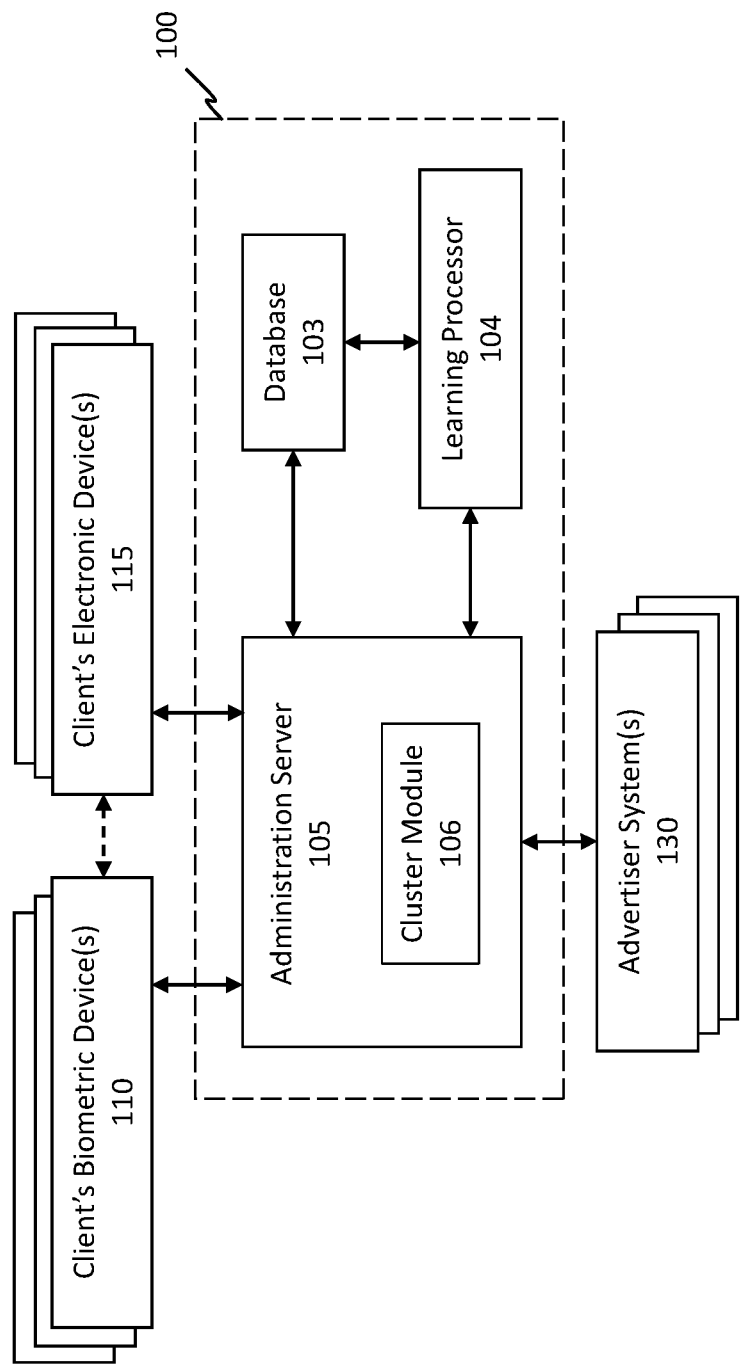
FIG. 1 depicts a system according to the present teachings.

The present teachings are described more fully hereinafter with reference to the accompanying drawings. The following description is presented for illustrative purposes only and the present teachings should not be limited to these embodiments. Any computer configuration and architecture satisfying the speed and interface requirements herein described may be suitable for implementing the system and method of the present embodiments.

In compliance with the statute, the present teachings have been described in language more or less specific as to structural and methodical features. It is to be understood, however, that the present teachings are not limited to the specific features shown and described, since the systems and methods herein disclosed comprise preferred forms of putting the present teachings into effect.

For purposes of explanation and not limitation, specific details are set forth such as particular architectures, interfaces, techniques, etc. in order to provide a thorough understanding. In other instances, detailed descriptions of well-known devices, circuits, and methods are omitted so as not to obscure the description with unnecessary detail.

Generally, all terms used in the claims are to be interpreted according to their ordinary meaning in the technical field, unless explicitly defined otherwise herein. All references to a/an/the element, apparatus, component, means, step, etc. are to be interpreted openly as referring to at least one instance of the element, apparatus, component, means, step, etc., unless explicitly stated otherwise. The steps of any method disclosed herein do not have to be performed in the exact order disclosed, unless explicitly stated. The use of "first," "second," etc. for different features/components of the present disclosure are only intended to distinguish the features/components from other similar features/components and not to impart any order or hierarchy to the features/components.

The present teachings disclose a system, a computer implemented method, an apparatus, and computer useable program product for providing customized Internet advertisements (or targeting online or in-app advertising) to a client. The system may have a database for storing a plurality of Internet advertisements and corresponding campaign information.

An electronic device according to the present teachings may include at least one of, for example, a desktop personal computer (PC), a laptop PC, a tablet PC, a smart phone, a mobile phone, a video phone, an e-book reader, a netbook computer, a workstation, a server, a personal digital assistant (PDA), a portable multimedia player (PMP), an MP3 player, a mobile medical device, a camera, a camcorder, or a wearable device including at least one of an accessory-type wearable device (e.g., a watch, glasses, or a head mounted device (HMD)), a textile/clothing integrated wearable device (e.g., electronic clothing), or a body-implantable wearable device (e.g., implantable circuit), but not limited thereto.

A biometric device according to the present teachings may include at least one of, for example, a desktop PC, a laptop PC, a tablet PC, a smart phone, a e-book reader, a smart watch, an activity tracker, a PDA, a PMP, an MP3 player, a mobile medical device, a camera, a camcorder, a smart home system including a center control hub and Internet of Things (IOT) devices such as a refrigerator, a water filtration system, a toilet, a mirror, a home security system (e.g., a doorbell, a lock, or a camera), a light switch, a temperature controller, an air quality system (e.g., a monitor or an alarm), but not limited thereto. For example, the laptop or smartphone may access a camera or a microphone thereof to recognize and collect data based on facial recognition, voice recognition, iris recognition, fingerprint, age analysis, and any demographic information. The laptop or smartphone may track the client's online behavior by using a "cookie." The smart watch or activity tracker may recognize and collect data based on sleep, travel, steps, heart rate, height, weight, and other personal biometrics. The smart watch or activity tracker may also track the client's location and gather information regarding the proximation and geographic optimization of the client's location. The refrigerator may detect the type of items stored in it such as food or beverage and keep track of the usage (consumption) and expiry (throwing away) of such items. The water filtration system may detect the water consumption. The toilet may detect urine and perform urine analysis. The mirror may include sensors that detect vein and skin conditions, such as dehydration. Other biometric information that may also be gathered by the biometric devices include eye movement, body temperature, breathing pattern, etc. In some embodiments, the biometric device may comprise hardware that detects and/or measures parameters representative of physiological, chemical, or behavioral characteristics of a person. Examples of the hardware include, but are not limited to, high-quality and robust touch/tactile sensors, heart rate sensors, cadence sensors (e.g., typing cadence sensors that measure keystroke dynamics, including speed, length of time between consecutive letters typed, and degree of impact on the keyboard; cycling cadence sensors that measure energy output in the form of rotations per minute), and GPS sensors for determining a person's location, altitude, velocity, etc. Signature recognition hardware may be used in and/or with a biometric device. For instance, static signature recognition hardware may comprise an optical scanner or camera that digitizes a signature (previously written on paper) and runs an algorithm that recognizes a person's text by way of analyzing its shape, center of gravity, edges and curves. Dynamic signature recognition hardware may comprise a graphics tablet or motion-sensitive stylus (e.g., stylus with inertial sensor) that acquires the person's handwriting in real-time and analyze the dynamically captured direction, stroke, pressure, and shape of the person's signature, thereby enabling reliable indication of the person's identity. In other embodiments, the biometric device may include a fingerprint sensor, finger recognition sensor, compact sensor that is configured to detect and store millions of repeated fingerprint readings, palm vein recognition sensor, ear recognition sensor, iris recognition and retina recognition sensor (e.g., near infrared camera technology), facial recognition system that measures multiple data points of a face, or voice recognition system that determines the identify of a speaker for accessing control. An accelerometer, gyroscope, compass, ambient light sensor, heartbeat sensor (e.g., optical heartbeat sensor), altimeter, and walk gait recognition system are other hardware components that may be incorporated into the biometric device for detecting characteristics of a person.

The platform according to the present teachings may include hardware, such as a computer or a server, or components thereof. The platform may provide an environment in which a piece of software is executed, such as a web page, an application, or a remote desktop.

When a client opens a website and sees an Internet advertisement provided by the system on the website, the client may click the Internet advertisement. If it is the first time this client clicks any Internet advertisement provided by the system, the system may output a message asking whether the client would like to opt in to provide biometric information assessed from biometric devices to the system to get a customized online advertising service.

If the client chooses to opt in, the system may ask the client to create an account by providing basic information such as user name and password and setting up the biometric devices. The system may detect any biometric devices nearby and provide a list of the detected biometric devices to the client so that the client can choose the biometric devices which belong to or are associated with the client and which should transmit the client's biometric information to the system. Alternatively, the system may use available information from any IOT and wearable device management system(s) provided by a third party to generate a list of the client's biometric devices, and allow the client to choose from that list.

After the initial opt-in setup of the biometric devices of the client, the system may receive biometric information or data of the client from the biometric devices of the client and store it in the database. The biometric information is data describing at least one of a plurality of physiological characteristics and behavioral characteristics of the customer, and the biometric information is gathered in real-time from any of the biometric devices of the client.

After the initial setup, when the client again opens a website, the system may collect receptivity information of the client responding to the Internet advertisement provided with the website. The receptivity information may include at least one of the number of click-throughs from the Internet advertisement, the number of purchasing events occurred from the Internet advertisement, or emotional characteristics of the client when viewing the Internet advertisement. For example, the system may count the number of click-throughs from the Internet advertisement, or the system may further track the client's online activity to check whether the client made a purchase after clicking through the Internet advertisement. As another example, the website may track the client's online activity through website cookies, including the number of click-throughs from the Internet advertisement and/or purchase events occurred due to the Internet advertisement, and the website may send the tracked activity information to the system. As another example, the system may monitor, through a camera, the client's facial expression or eye movement when the client opens a website to record the emotional characteristics of the client, and detect, at the same time, whether the client sees or clicks through the Internet advertisement. The system may receive and store the receptivity information of the client responding to the plurality of Internet advertisements. In some embodiments, the receptivity information may be obtained and/or derived from tracking URLs, which are normal URLs with a tracking token (UTM parameter) added to the end of it. When a client clicks on the tracking URL, the UTM parameter sends a signal indicating that the URL was clicked. In addition or alternatively, the receptivity information may be obtained and/or derived from tracking pixels (like Facebook Pixel). The tracking pixel is a 1 px by 1 px image that is placed in a display ad or on a webpage. When the tracking pixel loads, it sends a signal indicating that a client viewed the page. When used in conjunction with click-through data, tracking pixel data can provide further insight into receptivity. For example, if a banner ad with a tracking pixel is used, the system can analyze whether the client just viewed or actually clicked on the ad and thus evaluate how successful the ad is.

The system may include a processor that can access the database for the biometric information and the receptivity information. The processor may map the receptivity information to the biometric information, e.g., based on time. For example, when an amount of sleep is detected over the night, the receptivity information for the next day will be mapped to the biometric information of the sleep parameters of the night. Then, the processor may analyze the mapped information to generate customized marketing data. The customized marketing data may establish a relation between a receptivity probability for each of the plurality of Internet advertisements and a plurality of parameters representing the biometric information of the client. The customized marketing data may be in the form of a graph, or in the form of an equation, although not limited thereto. As in the sleep example, a graph of the customized marketing data may be established with sleep amount as X-axis and receptivity of a certain Internet advertisement as Y-axis.

The processor may calculate a receptivity probability for each of the plurality of Internet advertisements based on the customized marketing data by using current biometric state. The current biometric state may be the most recently received biometric information of the client over a certain time period, or real-time biometric information. For example, if the client had a certain amount of sleep last night, the receptivity probability for a certain Internet Advertisement is calculated as a point on Y-axis corresponding to the certain amount of sleep on X-axis based on the graph of the customized marketing data.

The processor may select an Internet advertisement from the plurality of Internet advertisements based on the calculated receptivity probabilities and output to the client the Internet advertisement through the client's electronic device. For example, if the calculated receptivity probability for Internet Advertisement 1 is 0.2, and the calculated receptivity probability for Internet Advertisement 2 is 0.8, the processor will select Internet Advertisement 2 between these two advertisements and transmit it to client through the client's electronic device. In some embodiments, the selected Internet advertisement has a receptivity probability greater than 0.70, and preferably greater than 0.80, and more preferably greater than 0.90.

Referring to FIG. 1, an advertising (or marketing) system 100 according to the present teachings may include a database 103, a learning processor 104, and an administration server 105. The administration server 105 may further include a cluster (or compiling) module 106. All main components can be located on different machines in different physical locations, or even run on a single machine. The advertising system 100 interacts with a client's electronic device 115 such as but not limited to a system on which standard Web browser software runs. The client's electronic device 115 first interacts with a web or app server (not shown) to get the access to the service provided by the advertising system 100. The advertising system 100 also interacts with a client's biometric devices upon authorization to get biometric information of the client. In addition, the advertising system 100 interacts with an advertiser system 130 such as but not limited to a system that provides a plurality of Internet advertisements and corresponding campaign information. The client's biometric devices 110, the client's electronic device 115, and the advertiser system 130 are connected to the administration server 105, which offers access to the database 103.

The administration server 105 handles initial requests for opt-in and requests from clients to deliver customized advertisements. The administration server 105 also handles the receptivity records of advertisements. The cluster module 106 in the administration server 105 collects biometric information of the client from the client's biometric devices upon authorization from the client. The administration server 105 contacts the database 103 in order to save and obtain the data relevant to provide the advertising service.

The administration server 105 also controls the access to the database 103 by the learning processor 104. The learning processor 104 may perform machine learning by mapping the biometric information and the receptivity information and analyzing the mapped information to generate customized marketing data for each client. The learning processor 104 periodically queries the files from the database 103 to obtain receptivity records of advertisements and biometric information of the client and adjusts a set of display weights accordingly. These weights are stored in the database 103, where the administration server 105 can access it during advertisement selection.

Upon a request for the service from the client through the client's electronic device 115, the administration server 105 calculates, based on the customized marketing data generated by the learning processor 104, a receptivity probability for each of the plurality of Internet advertisements as an output, by using current biometric state of the client as an input. The administration server 105 selects an Internet advertisement from the plurality of Internet advertisements based on the calculated receptivity probabilities, for example, selects the Internet advertisement with the largest receptivity probabilities. The administration server 105 outputs the selected Internet advertisement through the client's electronic device.

Figure 2:
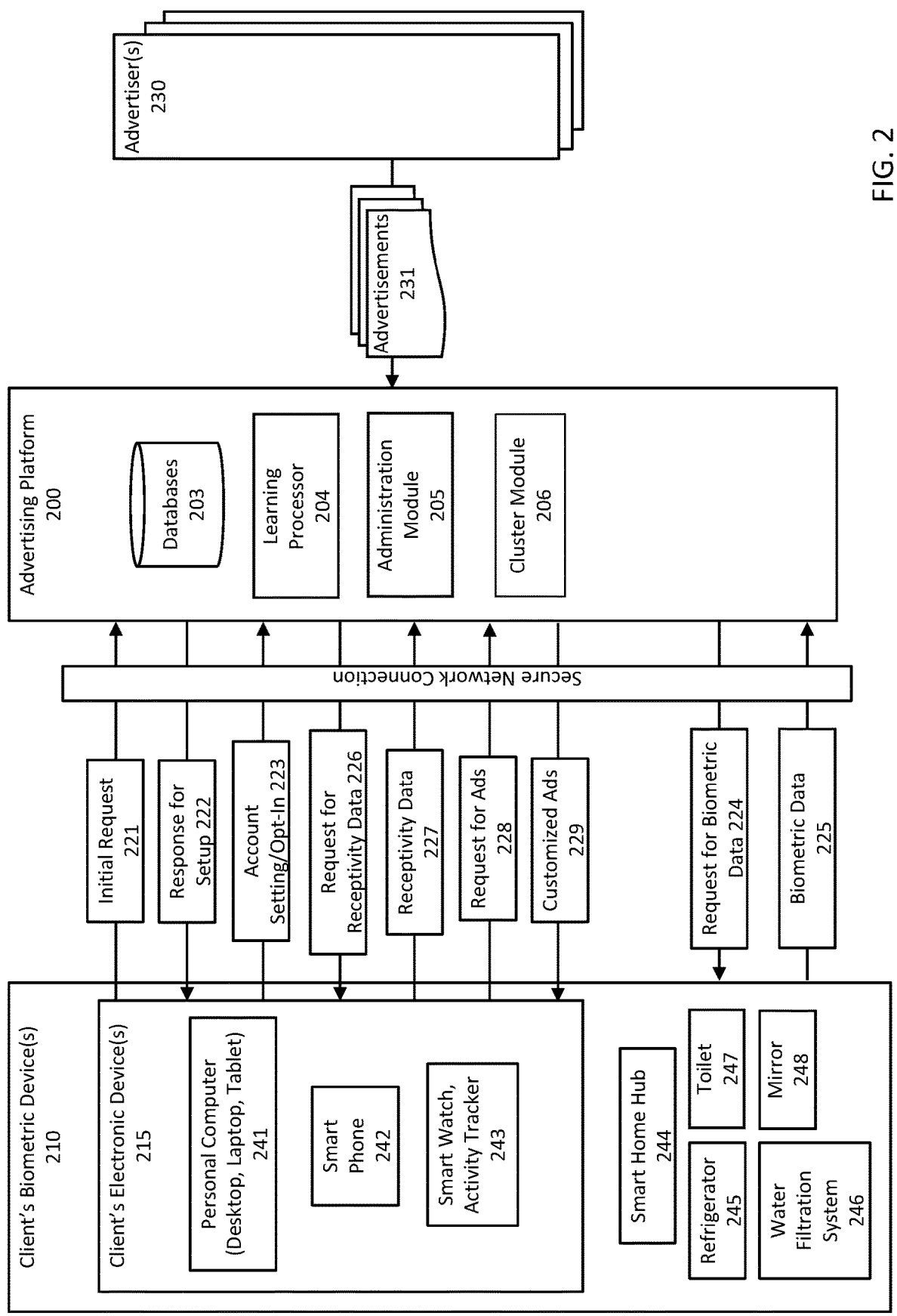
FIG. 2 depicts data flow of a system according to the present teachings.

Referring to FIG. 2, an advertising platform 200 according to the present teachings may include databases 203, a learning processor 204, an administration server 205, and a cluster module 206. The advertising platform 200 may provide functionality for targeting advertisements. The advertising platform 200 includes a number of additional modules providing additional functionality(ies), and may be part of the same software program or different software programs operating on different machines.

The databases 203 may include a database for storing a plurality of Internet advertisements and corresponding campaign information, a database for storing biometric information for each client, a database for storing receptivity records of advertisements for each client, a database for customized marketing data for each client resulted from machine learning based on the biometric information and the receptivity records.

The client's biometric device(s) 210 may include, for example, a client's electronic device 215, a smart home hub 244, a refrigerator 245, a water filtration system 246, a toilet 247, and a mirror 248. The client's electronic device(s) 215 may include a personal computer 241, a smart phone, a smart watch and/or activity tracker 243.

A client may use his electronic device 215 to establish a secure connection over the Internet and log on to the advertising platform 200. The advertising platform 200 may be offered as a service for delivering an advertisement or marketing message to the client. The advertising platform 200 may be provided through secure web pages, using an application, or even as a secure remote desktop connection, although not limited thereto. For example, a client opens a webpage on his computer and clicks a banner ad provided as the advertising service.

By logging on to the advertising platform, the client's electronic device 215 sends an initial request for the advertising service 221. The advertising platform 200 responds with a message for creating an account for the advertising service or for using an existing account of a third party for the advertising service, and sends the response 222 to the client's electronic device 215. The message asks whether the client would like to opt in a service that allows the advertising platform to access his biometric information collected by his biometric devices 210 and delivers customized advertisement using his biometric information. If the client chooses to opt in for the service, the advertising platform 200 may further ask the client to set up the biometric devices. For example, the advertising platform 200 may get or detect a list of devices and ask the client to choose which biometric devices are associated with the client and which of these devices the client wants the biometric information to be transmitted to the advertising platform.

The client's electronic device 215 selects to opt in and selects the biometric devices, and provides the information 223 for setting up an account including the selected biometric devices. Additional steps may be required to get authorization for each of the selected biometric devices, for example, from the biometric device's end or from a hub system managing the biometric devices. The administration module 205 may process the above information 223 and allow the cluster module 206 to gather the biometric information in real-time accompanying the related information regarding gathering. The biometric information is data describing at least one of a plurality of physiological characteristics and behavioral characteristics of the client, and it also includes time information and device information of the biometric data when gathered by the cluster module 206.

The cluster module 206 may send a request for biometric data and related information 224 to the client's biometric devices 210. The client's biometric devices 210 may send the requested information 225 to the cluster module 206. The cluster module 206 may save the biometric data and related information to the databases 203.

The administration module 205 or the cluster module 206 may collect receptivity records of advertisements of a client. For example, when the client browses a webpage or uses an App, the browser or the App may track online activity including viewing history or purchase history and may record receptivity of advertisements. The administration module 205 or the cluster module 206 may send a request for receptivity record of advertisements and related purchase history 226 to the client's electronic device 215. The client's electronic device 215 may send the requested data 227 to the administration module 205 or the cluster module 206. The administration module 205 or the cluster module 206 may save the receptivity data to the databases 203.

The learning processor 204 may access the databases 203 for the biometric data and the receptivity data. The learning processor 204 may analyze the data to generate customized marketing data for each client based on the biometric data and receptivity data. The customized marketing data for each client establishes a relation between biometric status and receptivity for each advertisement.

The administration module 205 may receive Internet advertisements or/and online campaign information 231 from advertisers' system 230 periodically, and save them to the databases 203. The learning processor 203 may also get access to the advertisement information for generating the customized marketing data for each client.

When the client's electronic device 215 establishes a secure connection over the Internet and logs on to the advertising platform 200 again, it sends a request for delivering the customized advisement(s) 228 to the advertising platform 200. For example, a client opens a webpage, which is accompanied with the online advertising service provided by the advertising platform 200, on the computer. By opening the webpage, the client's electronic device 215 sends a request for the online advertising service.

The administration module 205 may use the customized marketing data for the client and select an Internet advertisement from the plurality of Internet advertisements saved in the databases 203 based on the client's current biometric status. The administration module 205 may send the selected Internet advertisement 229 to the client's electronic device 215.

While the present teachings have been described above in terms of specific embodiments, it is to be understood that they are not limited to these disclosed embodiments. Many modifications and other embodiments will come to mind to those skilled in the art to which this pertains, and which are intended to be and are covered by this disclosure. It is intended that the scope of the present teachings should be determined by proper interpretation and construction of the disclosure and its legal equivalents, as understood by those of skill in the art relying upon this specification and the attached drawings.

What is claimed is:

1. An apparatus for providing customized advertisements, the apparatus comprising:
   a database,
      storing a plurality of electronic advertisements,
      receiving biometric information of a client from at least one biometric device of the client,
      receiving receptivity information of the client responding to the plurality of electronic advertisements; and
   a processor
      accessing the database,
      mapping the receptivity information to the biometric information, and analyzing the mapped information to generate customized marketing data, identifying a receptivity probability for each of the plurality of electronic advertisements based on the customized marketing data by using current biometric state of the client, selecting an electronic advertisement from the plurality of electronic advertisements based on the identified receptivity probabilities, and transmitting the selected electronic advertisement to a client electronic device, wherein the processor maps the biometric information and the receptivity information based on time;

wherein the biometric information received by the database includes an amount of sleep that the client received the night before, and wherein the processor maps the receptivity information of the following day to a sleep parameter of the night before; and wherein prior to the database receiving the biometric information and receiving the receptivity information, the processor is a configured to:

prompt the client to opt-in to receive customized advertising;

in response to the client accepting to receive customized advertising, detect the at least one biometric device in proximity to the client electronic device; and receive client input which indicates that the at least one biometric device belongs to or is associated with the client.

2. The apparatus of claim 1, wherein the biometric information includes data representing at least one physiological characteristic or behavioral characteristic of the client, and
   wherein the biometric information is gathered in real-time.

3. The apparatus of claim 1, wherein the receptivity information includes at least one of a number of click-throughs from the electronic advertisements or a number of purchasing events from the electronic advertisements.

4. The apparatus of claim 1, wherein the receptivity information includes emotional characteristics of the client when viewing the electronic advertisements.

5. The apparatus of claim 4, wherein the emotional characteristics include at least one image of a facial expression or eye movement of the client, and wherein the database receives the at least one image from a camera associated with the client.

6. The apparatus of claim 5, wherein the processor comprises facial recognition that analyzes the at least one image to detect and assess an emotion or mood of the client.

7. The apparatus of claim 1, wherein the processor generates the customized marketing data by determining a relation between a receptivity probability for each of the plurality of electronic advertisements and a plurality of parameters representing the biometric information of the client, and
   wherein the current biometric state of the client includes at least one of the plurality of parameters representing the biometric information of the client in real time or most recently received.

8. The apparatus of claim 1, wherein the processor detects a plurality of biometric devices and provides a list of the detected biometric devices to the client, and wherein the processor receives client feedback indicating which of the plurality of biometric devices are associated with the client and should transmit the biometric information of the client to the database.

9. The apparatus of claim 1, wherein the biometric information includes heartbeat data, sleep pattern data, steps taken by the client, location data, water intake data, and/or food intake data.

10. The apparatus of claim 1, wherein the processor selects the electronic advertisement having the highest receptivity probability among the plurality of electronic advertisements.

11. A system for providing customized advertisements to a client, the system comprising:

an advertising platform having a database, a processor, and an administration server, the advertising platform configured to interact with a client electronic device and a client biometric device;

a plurality of advertiser systems in communication with the advertising platform, each advertiser system containing at least one electronic advertisement of an advertiser;

in response to client authorization, the database receives biometric information of the client from the client biometric device and receives receptivity information of the client responding to a plurality of electronic advertisements;

the processor maps the receptivity information to the biometric information and analyzes the mapped information to generate customized marketing data;

the administration server identifies a receptivity probability for each of the plurality of electronic advertisements based on the customized marketing data by using current biometric state of the client and selects an electronic advertisement from the plurality of electronic advertisements based on the identified receptivity probabilities; and the advertising platform transmits the selected electronic advertisement to the client electronic device for display in a web browser or application;

wherein the processor maps the biometric information and the receptivity information based on time;

wherein the biometric information received by the database includes an amount of sleep that the client received the night before, and wherein the processor maps the receptivity information of the following day to a sleep parameter of the night before; and wherein prior to the database receiving the biometric information and receiving the receptivity information, the processor is a configured to:

prompt the client to opt-in to receive customized advertising;

in response to the client accepting to receive customized advertising, detect the client biometric device in proximity to the client electronic device; and receive client input which indicates that the client biometric device belongs to or is associated with the client.

12. The system of claim 11, wherein the administration server is connected to the advertiser systems and provides access between the database and the advertiser systems.

13. The system of claim 11, wherein the processor utilizes machine learning to map the biometric information and the receptivity information.

14. The system of claim 13, wherein the processor obtains receptivity information and biometric information to adjust a set of weights, wherein said weights are used in selecting the electronic advertisement.

15. The system of claim 11, wherein the database is configured to receive the biometric information from the client electronic device, a smart home hub, a refrigerator, a water filtration system, a toilet, and/or a mirror.

16. A system for providing customized advertisements to a client, the system comprising:
- an advertising platform having a database, a processor, and an administration server, the advertising platform configured to interact with a client electronic device and a client biometric device;
- a plurality of advertiser systems in communication with the advertising platform, each advertiser system containing at least one electronic advertisement of an advertiser;
- in response to client authorization, the database receives biometric information of the client from the client biometric device and receives receptivity information of the client responding to a plurality of electronic advertisements;
- the processor maps the receptivity information to the biometric information and analyzes the mapped information to generate customized marketing data;
- the administration server identifies a receptivity probability for each of the plurality of electronic advertisements based on the customized marketing data by using current biometric state of the client and selects an electronic advertisement from the plurality of electronic advertisements based on the identified receptivity probabilities; and
- the advertising platform transmits the selected electronic advertisement to the client electronic device for display in a web browser or application;
- wherein the selected electronic advertisement has the highest identified receptivity probability;
- wherein the processor maps the biometric information and the receptivity information based on time;
- wherein the biometric information received by the database includes an amount of sleep that the client received the night before, and wherein the processor maps the receptivity information of the following day to a sleep parameter of the night before; and
- wherein prior to the database receiving the biometric information and receiving the receptivity information, the processor is a configured to:
- prompt the client to opt-in to receive customized advertising;
- in response to the client accepting to receive customized advertising, detect the client biometric device in proximity to the client electronic device; and
- receive client input which indicates that the client biometric device belongs to or is associated with the client.

17. The system of claim 16, wherein the biometric information includes data representing at least one physiological characteristic or behavioral characteristic of the client, and wherein the biometric information is gathered in real-time.

18. A method of providing customized advertisements to a client, comprising:
- obtaining biometric data of the client from at least one biometric device of the client;
- transmitting the biometric data to a database of an advertising platform for storage;
- collecting receptivity information of the client responding to one or more electronic advertisements provided in a website, which is displayed on an electronic device of the client;
- transmitting the receptivity information from the electronic device to the database for storage;
- mapping, via a processor of the advertising platform, the receptivity information to the biometric data to generate customized marketing data;
- obtaining a recent biometric state of the client from the at least one biometric device and using the recent biometric state to identify a receptivity probability for each of a plurality of electronic advertisements based on the customized marketing data;
- selecting one of the plurality of electronic advertisements which has the highest receptivity probability; and
- transmitting the selected electronic advertisement to the client;
- wherein said mapping via the processor is based on time;
- wherein the biometric data received by the database includes an amount of sleep that the client received the night before, and wherein the processor maps the receptivity information of the following day to a sleep parameter of the night before; and
- wherein prior to the steps of obtaining the biometric data and collecting the receptivity information, the method comprises:
- prompting the client to opt-in to receive customized advertising;
- in response to the client accepting to receive customized advertising, detecting the at least one biometric device in proximity to the electronic device; and
- receiving client input which indicates that the at least one biometric device belongs to or is associated with the client.

19. The method of claim 18, wherein the highest receptivity probability is greater than 0.70.

* * * * *